United States Patent [19]

Minderhoud et al.

[11] Patent Number: 4,507,404
[45] Date of Patent: Mar. 26, 1985

[54] PREPARATION OF HYDROCARBON MIXTURES FROM SYNGAS

[75] Inventors: Johannes K. Minderhoud; Martin F. M. Post, both of Amsterdam, Netherlands

[73] Assignee: Shell Oil Company, Houston, Tex.

[21] Appl. No.: 583,478

[22] Filed: Feb. 24, 1984

[30] Foreign Application Priority Data

Mar. 10, 1983 [NL] Netherlands ..................... 8300873

[51] Int. Cl.$^3$ ............................................. C07C 1/04
[52] U.S. Cl. ................................. 518/714; 518/713; 518/728; 502/61; 502/63; 502/243; 502/250
[58] Field of Search ..................... 518/713, 714, 728

[56] References Cited

U.S. PATENT DOCUMENTS

| | | | |
|---|---|---|---|
| 4,086,262 | 4/1978 | Chang et al. | 518/714 |
| 4,338,089 | 7/1982 | Schaper et al. | 518/728 |
| 4,385,193 | 5/1983 | Bijwaard et al. | 518/73 |

FOREIGN PATENT DOCUMENTS

| | | |
|---|---|---|
| 2006260 | 5/1979 | United Kingdom . |
| 2037315 | 7/1980 | United Kingdom . |

*Primary Examiner*—Howard T. Mars
*Attorney, Agent, or Firm*—Dean F. Vance

[57] ABSTRACT

A process is described for preparing gasoline boiling range hydrocarbons with a high iso-paraffins content from syngas having a $H_2/CO$ mol. ratio between 1.0 and 5.0 over a catalyst mixture comprising a methanol synthesis component which contains zinc and one or more metals selected from the group consisting of chromium, copper and aluminum and a crystalline metal silicate with ZSM-5 structure which contains $SiO_2$ and one or more oxides of a trivalent metal A selected from the group consisting of aluminum, iron, gallium, rhodium, chromium and scandium, and wherein the $SiO_2/A_2O_3$ molar ratio is higher than 10; and which catalyst mixture has been prepared by spray-drying followed by calcining at a temperature between 425° and 525° C.

10 Claims, No Drawings

PREPARATION OF HYDROCARBON MIXTURES FROM SYNGAS

BACKGROUND OF THE INVENTION

The invention relates to a process for the preparation of a hydrocarbon mixture from a mixtures of carbon monoxide and hydrogen.

Mixtures of carbon monoxide and hydrogen can be converted into hydrocarbon mixtures by using a mixture of two catalysts which has been prepared by dispersing a crystalline metal silicate of a special structure in water together with one or more precipitates in which zinc and one or more metals chosen from chromium, copper and aluminum occur and which precipitates have been prepared by adding a basic reacting substance to one or more aqueous solutions of salts of the metals involved, spray-drying the dispersion thus obtained and calcining the spray-dried material. Said crystalline metal silicates are characterized in that after one hour's calcination in air at 500° C. they have the following properties:

(a) an X-ray powder diffraction pattern in which the four lines mentioned in Table A are the strongest lines, Table A d(Å)

11.1±0.2
10.0±0.2
3.84±0.07
3.72±0.06; and (b) in which, in addition to $SiO_2$, one or more oxides of a trivalent metal A chosen from aluminum, iron, gallium, rhodium, chromium and scandium occur, the $SiO_2/A_2O_3$ molar ratio is higher than 10.

Thus far the calcination temperatures used in the preparation of these catalyst mixtures were temperatures below 425° C. and they were used for the conversion of $H_2/CO$ mixtures having a $H_2/CO$ molar ratio lower than 1. In this manner a hydrocarbon mixture can be obtained whose $C_5^+$ fraction consists more than 50%w of aromatics. Although as a result of the high aromatics concentration the $C_5^+$ fraction has a high octane number, it is not very suitable for use as motor gasoline since the components having a high octane number occur substantially in the higher boiling part of the fraction. A good motor gasoline requires a uniform distribution of components having a high octane number over the entire boiling range of the gasoline, which means that the gasoline should also contain a considerable concentration of low-boiling components having a high octane number, notably branched $C_5$ and $C_6$ paraffins. For use as motor gasoline there is special interest in $C_5$ and $C_6$ paraffins. For preparing hydrocarbon mixtures whose $C_5^+$ fractions meet this requirement the above-described process such as it was carried out heretofore is not suitable, as may be seen from the following example. Starting from a $H_2/CO$ mixture having a $H_2/CO$ molar ratio of 0.5 and using a conversion temperature of 380° C. and a catalyst mixture calcined at 400° C., a hydrocarbon mixture was obtained whose $C_5^+$ fraction contained about 75%w of aromatics and no more than 5%w of branched $C_5$ and $C_6$ paraffins.

An investigation was carried out to determine whether it is possible to prepare hydrocarbon mixtures whose $C_5^+$ fractions have the desired high content of branched $C_5$ and $C_6$ paraffins by modifying the above-described process. To this end it was examined what effect the conversion temperature has on the composition of the $C_5^+$ fraction of the hydrocarbon mixture. Starting from the afore-mentioned $H_2/CO$ mixture having a $H_2/CO$ molar ratio of 0.5 and using the afore-mentioned catalyst mixture calcined at 400° C. there was produced, by raising the conversion temperature from 380° to 400° C., a hydrocarbon mixture whose $C_5^+$ fraction contained about 65%w aromatics and about 12%w branched $C_5$ and $C_6$ paraffins. From this it is seen that raising the conversion temperature has created a shift within the product composition in the desired direction. With an eye to the desired content of branched $C_5$ and $C_6$ paraffins, which is higher than 40%w, this shift is insufficient. Attempts to achieve the desired end by raising the conversion temperature further have proved unsuccessful, since this measure causes an unacceptable drop in selectivity towards liquid product as well as very rapid catalyst deactivation.

Continued research has revealed that the branched $C_5$ and $C_6$ paraffins content of the $C_5^+$ fraction is dependent to a considerable extent on the temperature at which the catalyst mixture has been calcined. Starting from the afore-mentioned $H_2/CO$ mixture having a $H_2/CO$ molar ratio of 0.5 and using the afore-mentioned catalyst mixture which now had been calcined at a temperature between 425° and 525° C. instead of at 400° C., there could be obtained at a conversion temperature of 400° C. a product whose content of branched $C_5$ and $C_6$ paraffins had increased about twofold. Upon further research it was found that the branched $C_5$ and $C_6$ paraffins content of the $C_5^+$ fraction is also dependent to a great extent on the $H_2/CO$ molar ratio of the feed. Starting from the $H_2/CO$ mixture having a $H_2/CO$ molar ratio between 1.0 and 5.0 instead of 0.5 and using the afore-mentioned catalyst mixture calcined at 400° C., there could be obtained at a conversion temperature of 400° C. a product whose content of branched $C_5$ and $C_6$ paraffins—just as in the experiment using the catalyst mixture calcined at a higher temperature—had increased about twofold.

Although the two above-mentioned measures lead to a considerable improvement on the situation described earlier where, by using a catalyst mixture calcined at 400° C. and starting from a feed having a $H_2/CO$ molar ratio of 0.5, a product was obtained whose $C_5^+$ fraction had a content of branched $C_5$ and $C_6$ paraffins of about 12%w, neither of these measures is capable of yielding a product whose $C_5^+$ fraction has the desired high content of branched $C_5$ and $C_6$ paraffins. Nor is it to be expected—in view of the fact that the two measures bear no relation to one another and considering the extent of the rise in branched $C_5$ and $C_6$ paraffins content of the $C_5^+$ fraction which can be attained by each of these measures separately—that applying the two measures simultaneously will lead to the achievement of the desired end. Nevertheless this combination was also included as part of the investigation. This led to the surprising finding that by combining the two measures a product can be prepared whose $C_5^+$ fraction amply meets the requirements. Starting from a feed having a $H_2/CO$ molar ratio between 1.0 and 5.0 and using the catalyst mixture calcined at a temperature between 425° and 525° C. mentioned hereinbefore it proved possible, at a conversion temperature of 400° C., to prepare a product whose $C_5^+$ fraction had a content of branched $C_5$ and $C_6$ paraffins of about 50%w, viz. more than four times the content obtained by using the feed with a lower $H_2/CO$ molar ratio and the catalyst mixture calcined at a lower temperature.

SUMMARY OF THE INVENTION

The present patent application therefore relates to a process for the preparation of a hydrocarbon mixture from a mixture of carbon monoxide and hydrogen in which in order to prepare a hydrocarbon mixture whose $C_5+$ fraction has a high content of branched $C_5$ and $C_6$ paraffins, a $H_2/CO$ mixture having a $H_2/CO$ molar ratio between 1.0 and 5.0 is contacted with a catalyst mixture which has been prepared by dispersing a crystalline metal silicate having the properties mentioned hereinbefore under (a) and (b) in water together with one or more of the afore-mentioned zinc-containing precipitates, spray-drying the dispersion thus obtained and calcining the spray-dried material at a temperature between 425° and 525° C.

DETAILED DESCRIPTION OF THE INVENTION

Spray-drying is a method which for many years has been used on a commercial scale for preparing small globular particles from a solid material or a mixture of solid materials. The process is carried out by atomizing a dispersion in water of the material to be spray-dried through a nozzle or from a rotating disc into a hot gas. The process is particularly suitable for bringing about a very intimate contact between different materials. On account of their form, size and strength the catalyst particles produced by spray-drying are very suitable for use in the fluidized state.

Although according to the invention crystalline silicates containing more than one metal A can be used, preference is given to the use of silicates in which only one metal A is present and in particular to silicates comprising aluminum, iron or gallium as metal A. The crystalline silicates should have a $SiO_2/A_2O_3$ molar ratio which is higher than 10. Preference is given to the use of silicates with a $SiO_2/A_2O_3$ molar ratio lower than 1000 and in particular between 20 and 500. The crystalline silicates are defined, among other things, by the X-ray powder diffraction pattern which they display after one hour's calcination in air at 500° C. In this pattern the strongest lines should be the four lines mentioned in Table A. The complete X-ray powder diffraction pattern of a typical example of the present crystalline silicates after one hour's calcination in air at 500° C. is given in Table B.

TABLE B

| d(Å) | Rel. int. | d(Å) | Rel. int. |
|---|---|---|---|
| 11.1 | 100 | 3.84 (D) | 57 |
| 10.0 (D) | 70 | 3.72 (D) | 31 |
| 8.93 | 1 | 3.63 | 16 |
| 7.99 | 1 | 3.47 | <1 |
| 7.42 | 2 | 3.43 | 5 |
| 6.68 | 7 | 3.34 | 2 |
| 6.35 | 11 | 3.30 | 5 |
| 5.97 | 17 | 3.25 | 1 |
| 5.70 | 7 | 3.05 | 8 |
| 5.56 | 10 | 2.98 | 11 |
| 5.35 | 2 | 2.96 | 3 |
| 4.98 (D) | 6 | 2.86 | 2 |
| 4.60 | 4 | 2.73 | 2 |
| 4.35 | 5 | 2.60 | 2 |
| 4.25 | 7 | 2.48 | 3 |
| 4.07 | 2 | 2.40 | 2 |

TABLE B-continued

| d(Å) | Rel. int. | d(Å) | Rel. int. |
|---|---|---|---|
| 4.00 | 4 | | |

(D) = doublet

The crystalline silicates can be prepared starting from an aqueous mixture comprising the following compounds: one or more silicon compounds, one or more compounds which contain a monovalent organic cation (R) or from which such a cation is formed during the preparation of the silicate, one or more compounds in which a trivalent metal A is present and optionally one or more compounds of an alkali metal (M). The preparation is carried out by maintaining the mixture at an elevated temperature until the silicate has formed and subsequently separating the silicate crystals from the mother liquor and washing, drying and calcining the crystals. In the aqueous mixture from which the silicates are prepared the various compounds should be present in the following ratios expressed in moles of the oxides:
$M_2O: SiO_2 < 0.35$,
$R_2O: SiO_2 = 0.01-0.5$,
$SiO_2: A_2O_3 > 10$ and
$H_2O: SiO_2 = 5-100$.

If in the preparation of the crystalline silicates the starting material is an aqueous mixture in which one or more alkali metal compounds are present, the crystalline silicates obtained will contain alkali metal. Depending on the concentration in which the alkali metal compounds are present in the aqueous mixture, crystalline silicates may be obtained which contain more than 1%w of alkali metal. Since the presence of alkali metal in the crystalline silicates has an adverse effect on their catalytic properties, it is common practice in case of crystalline silicates with a relatively high alkali metal content to reduce this content before using the silicates as catalysts. A reduction of the alkali metal content to about 200 ppmw is sufficient for the purpose. It has been found that a further reduction of the alkali metal content has virtually no more effect on the catalytic properties of the silicate. Reduction of the alkali metal content of crystalline silicates can very suitably be effected by treating the silicates once or several times with a solution of an ammonium compound. Alkali metal ions are then exchanged for $NH_4+$ ions and the silicate is converted to the $NH_4+$ form. By calcination the $NH_4+$ form of the silicate is converted to the $H+$ form.

In the preparation of the catalyst mixtures used in the process according to the invention use is made of one or more precipitates in which zinc occurs together with one or more of the metals chromium, aluminum and copper and which precipitates have been obtained by adding a basic reacting material to one or more aqueous solutions of salts of the metals involved. Examples of metal combinations eligible for being introduced into the catalyst mixtures to be prepared by spray-drying via the precipitates are zinc-chromium, zinc-chromium-copper and zinc-aluminum-copper. Preference is given to the use of precipitates in which, in addition to zinc, chromium is present, in particular precipitates in which the atomic percentage of zinc, calculated on the sum of zinc and chromium, is at least 60% and in particular 60–80%. The metal-containing precipitates which are dispersed in water together with the crystalline silicate may be prepared by precipitation of each metal individually, or by co-precipitation of the desired metal combination. Preference is given to the use of a co-precipitate obtained by adding a basic reacting material to an aqueous solution containing all the metals involved.

As regards the ratio between the quantities of metal-containing precipitate and crystalline silicate in the dispersion from which the catalyst mixture is prepared by spray-drying, this ratio is preferably chosen such that a catalyst mixture is obtained which per pbw of silicate comprises 0.5-10, and more particularly 1-7.5, pbw of metal oxides coming from the precipitate.

In the process according to the invention a $H_2/CO$ mixture is converted into a hydrocarbon mixture whose $C_5^+$ fraction has a high content of branched $C_5$ and $C_6$ paraffins. Suitable conditions for carrying out the process are a temperature of 200°-500° C. and in particular of 300°-450° C., a pressure of 1-150 bar and in particular of 5-100 bar and a space velocity of 50-5000 and in particular of 300-3000 N1 gas/l catalyst/hour.

The process according to the invention may very suitably be carried out as an independent process in which the conversion of the $H_2/CO$ mixture is effected in one step. If desired, unconverted synthesis gas can be recirculated. The process according to the invention may also very suitably be used as part of the multi-stage process for the conversion of $H_2/CO$ mixtures into hydrocarbon mixtures. In that case two options are available, viz.

(a) the process may be used as the first step of a two-step process in which carbon monoxide and hydrogen present in the reaction product of the first step are contacted—together with other components of said reaction product, if desired—in a second step with a catalyst comprising activity for the conversion of a $H_2/CO$ mixture into paraffinic hydrocarbons, which metal components have been chosen from the group formed by cobalt, nickel and ruthenium, (b) the process may be used as the first step in a three-step process in which the first two steps are carried out as stated under (a) and in which the catalyst used in the second step is a zirconium-, titanium- or chromium-promoted cobalt catalyst supported on silica as a carrier, which catalyst has been prepared by impregnation and/or kneading. In this three-step process advantage is taken of the fact that the high-boiling part of the reaction product of the second step can be converted in high yield into middle distillates by a catalytic hydrotreatment.

The three-step process mentioned under (b) comprises carrying out a catalytic hydrotreatment as a third step following the two-step process mentioned under (a). As feed for the catalytic hydrotreatment at least the part of the reaction product of the second step is chosen whose initial boiling point lies above the final boiling point of the heaviest middle distillate desired as end product. The hydrotreatment, which is characterized by a very low hydrogen consumption, yields middle distillates having a considerably lower pour point than those obtained in the direct conversion of a $H_2/CO$ mixture according to Fischer-Tropsch. Catalysts very suitable for carrying out the catalytic hydrotreatment are those which comprise one or more noble metals of Group VIII of the Periodic Table supported on a carrier.

The invention is now illustrated with the aid of the following example.

EXAMPLE

Catalyst preparation

Preparation of a Zn/Cr co-precipitate $Zn(NO_3)_2.6H_2O$ and $Cr(NO_3)_3.9H_2O$ were dissolved in water in such quantities that a Zn/Cr solution was obtained in which the $Zn/(Zn+Cr)$ atomic ratio was 0.67. Together with a stoichiometric quantity of a 10% aqueous $NH_3$ solution said solution was pumped with stirring through a mixing unit which was kept at a temperature of 20° C. The Zn/Cr co-precipitate obtained was collected and left to age with stirring for one hour at 20° C. The solid material was filtered off and washed with water until the wash water was free from $NO_3^-$ ions.

Preparation of an aluminum silicate catalyst component

The starting material was a crystalline aluminum silicate which after one hour's calcination in air at 500° C. had the following properties:
(a) an X-ray powder diffraction pattern substantially corresponding with that given in Table B, and
(b) a $SiO_2/Al_2O_3$ molar ratio of 290.

From this crystalline aluminum silicate the aluminum silicate catalyst component was prepared by boiling with a 1.0 molar $NH_4NO_3$ solution, washing with water, drying at 120° C. for 16 hours and calcination in air at 500° C. for one hour.

Catalyst mixtures I-III

The aluminum silicate catalyst component prepared in the manner described hereinbefore was dispersed in water by using a turbostirrer. To the dispersion thus obtained such a quantity of the Zn/Cr co-precipitate prepared in the manner described hereinbefore was added with stirring that the weight ratio of $ZnO+Cr_2O_3$ to the silicate in the dispersion was 5:1. Finally, sufficient water was stirred into the dispersion that its content of solid matter was 15%w. Sedimentation of the dispersion was prevented by continuous stirring. The dispersion thus obtained was spray-dried in air in counter-current operation using compressed air. The air inlet temperature was 300° C. and the air outlet temperature was 120° C. Catalyst mixtures I, II and III were prepared from the material thus obtained by calcination in air for one hour at 400°, 500° and 550° C., respectively.

Catalyst mixtures I-III were tested for the preparation of hydrocarbon mixtures from $H_2/CO$ mixtures. These tests were carried out in a vertically disposed fluidized-bed reactor of 175 cm depth and 500 ml volume containing about 300 ml catalyst. $H_2/CO$ mixtures of various $H_2/CO$ molar ratios were contacted with catalyst mixtures I-III at a pressure of 60 bar, a superficial gas rate of 1.3 cm/s (corresponding to a space velocity of about 85 $Nl.kg^{-1}.h^{-1}$) and at various temperatures. The results of these experiments, averaged over the first 50 hours, are given in Table C.

TABLE C

| Experiment, No. | 1 | 2 | 3 | 4 | 5 | 6 | 7 |
|---|---|---|---|---|---|---|---|
| Catalyst mixture, No. | I | I | II | III | I | II | III |
| Temperature at which catalyst mixture was calcined, °C. | 400 | 400 | 500 | 550 | 400 | 500 | 550 |
| $H_2/CO$ molar ratio | 0.5 | 0.5 | 0.5 | 0.5 | 1.4 | 1.44 | 1.44 |

TABLE C-continued

| Experiment, No. | 1 | 2 | 3 | 4 | 5 | 6 | 7 |
|---|---|---|---|---|---|---|---|
| of feed |  |  |  |  |  |  |  |
| Reaction temperature °C. | 380 | 400 | 400 | 400 | 400 | 400 | 400 |
| Conversion of synthesis gas, % v | 55 | 65 | 66 | 67 | 60 | 61 | 61 |
| $C_3^+$ selectivity calculated on $C_1^+$, % w | 94 | 92 | 92 | 86 | 89 | 87 | 82 |
| $C_5^+$ selectivity calculated on $C_1^+$, % w | 82 | 70 | 66 | 60 | 66 | 63 | 55 |
| Composition of $C_5^+$ product, % w |  |  |  |  |  |  |  |
| paraffins | 10 | 17 | 34 | 20 | 30 | 60 | 44 |
| branched $C_5$ and $C_6$ paraffins | 5 | 12 | 25 | 11 | 23 | 50 | 23 |
| naphthenes | 15 | 18 | 16 | 27 | 24 | 17 | 34 |
| aromatics | 75 | 65 | 50 | 53 | 46 | 23 | 22 |

Of the experiments mentioned in Table C only Experiment 6 is an experiment according to the invention. In this experiment a catalyst mixture which had been calcined at a temperature between 425° and 525° C. was used for the conversion of a feed having a $H_2/CO$ molar ratio between 1.0 and 5.0, and a hydrogen mixture was obtained whose $C_5^+$ fraction had a content of branched $C_5$ and $C_6$ paraffins of more than 40%w. The other experiments fall outside the scope of the invention. They have been included for comparison. In Experiments 1 and 2 a catalyst mixture which had been calcined at a temperature lower than 425° C. was used for the conversion of a feed having a $H_2/CO$ molar ratio lower than 1.0. In Experiment 3 the feed had a $H_2/CO$ molar ratio lower than 1.0. In Experiment 4 a catalyst mixture which had been calcined at a temperature higher than 525° C. was used for the conversion of a feed having a $H_2/CO$ molar ratio lower than 1.0. In Experiment 5 a catalyst mixture was used which had been calcined at a temperature below 425° C. In Experiment 7 a catalyst mixture was used which had been calcined at a temperature higher than 525° C. In Experiments 1-5 and 7 a hydrogen mixture was obtained whose $C_5^+$ fraction had a content of $C_5$ and $C_6$ paraffins lower than 40%w.

What is claimed is:

1. A process for the preparation of a hydrocarbon mixture from a mixture of carbon monoxide and hydrogen, characterized in that for the preparation of a hydrocarbon mixture whose $C_5^+$ fraction has a high content of branched $C_5$ and $C_6$ paraffins, a $H_2/CO$ mixture having a $H_2/CO$ molar ratio between 1.0 and 5.0 is contacted with a catalyst mixture which has been prepared by dispersing a crystalline metal silicate which after one hour's calcination in air at 500° C. has the following properties:

(a) an X-ray powder diffraction pattern in which the strongest lines are the four lines given in Table A Table A
   d(Å)

11.1±0.2
   10.0±0.2
   3.84±0.07
   3.72±0.06; and (b) in which, in addition to $SiO_2$, one or more oxides of a trivalent metal A chosen from aluminum, iron, gallium, rhodium, chromium and scandium occur, the $SiO_2/A_2O_3$ molar ratio is higher than 10;

in water together with one or more precipitates which contain zinc and one or more metals chosen from chromium, copper and aluminum and which precipitates have been obtained by adding a basic reacting substance to one or more aqueous solutions of salts of the metals concerned, spray-drying the dispersion thus obtained and calcining the spray-dried material at a temperature between 425° and 525° C.

2. A process as claimed in claim 1, characterized in that the catalyst mixture has been prepared by using a crystalline silicate comprising only one trivalent metal A chosen from the group consisting of aluminum, iron and gallium.

3. A process as claimed in claim 1, characterized in that the catalyst mixture has been prepared by using a crystalline silicate having a $SiO_2/A_2O_3$ molar ratio between 20 and 500.

4. A process as claimed in claim 2, characterized in that the catalyst mixture has been prepared by using a crystalline silicate having a $SiO_2/A_2O_3$ molar ratio between 20 and 500.

5. A process as claimed in claim 1, characterized in that the catalyst mixture has been prepared by using a co-precipitate obtained by adding a basic reacting substance to an aqueous solution comprising all the metals involved.

6. A process as claimed in claim 3, characterized in that the catalyst mixture has been prepared by using a co-precipitate obtained by adding a basic reacting substance to an aqueous solution comprising all the metals involved.

7. A process as claimed in claim 1, characterized in that in the catalyst mixture has been prepared by using a precipitate which, in addition to zinc, comprises chromium and in which the atomic percentage of zinc calculated on the sum of zinc and chromium is 60-80%.

8. A process as claimed in claim 5, characterized in that in the catalyst mixture has been prepared by using a precipitate which, in addition to zinc, comprises chromium and in which the atomic percentage of zinc calculated on the sum of zinc and chromium is 60-80%.

9. A process as claimed in claim 1, characterized in that in the preparation of the catalyst mixture the ratio between the quantities of metal-containing precipitate and crystalline silicate in the dispersion is chosen such that after spray-drying a catalyst mixture is obtained which per part by weight of silicate comprises 1-7.5 pbw of metal oxides coming from the precipitate.

10. A process as claimed in claim 7, characterized in that in the preparation of the catalyst mixture the ratio between the quantities of metal-containing precipitate and crystalline silicate in the dispersion is chosen such that after spray-drying a catalyst mixture is obtained which per part by weight of silicate comprises 1-7.5 pbw of metal oxides coming from the precipitate.

* * * * *